United States Patent [19]

Nishida et al.

[11] Patent Number: 4,851,558
[45] Date of Patent: Jul. 25, 1989

[54] PROCESS FOR PRODUCING ALKOXYSILANES

[75] Inventors: Makoto Nishida; Hiroaki Hanaoka, both of Ohta, Japan

[73] Assignee: Toshiba Silicone Co., Ltd., Tokyo, Japan

[21] Appl. No.: 199,562

[22] Filed: May 27, 1988

[30] Foreign Application Priority Data

Jun. 12, 1987 [JP] Japan .................................. 62-145378

[51] Int. Cl.$^4$ .............................................. C07F 7/18
[52] U.S. Cl. .................................................. 556/471
[58] Field of Search ........................................ 556/471

[56] References Cited

U.S. PATENT DOCUMENTS 4,228,092 10/1980 Kotzsch et al. ................. 556/422
4,421,926 12/1983 Tolentino ......................... 556/471
4,642,363 2/1987 Groh et al. ....................... 556/471

*Primary Examiner*—Paul F. Shaver

[57] ABSTRACT

In a process for producing an alkoxysilane represented by general formula (III):

$$(CH_3)_a H_b Si(OR)_c Cl_{4-(a+b+c)} \qquad (III)$$

wherein a represents a number of 0 to 2, b represents a number of 1 to 3, c represents a number of 0 to 2, the sum of a+b+c represents a number of not greater than 4 which comprises reacting a chlorosilane represented by general formula (I):

$$(CH_3)_a H_b SiCl_{4-(a+b)} \qquad (I)$$

wherein a and b have the same meanings as described above and a+b represents a number of less than 4, with an alcohol represented by general formula (II);

$$ROH \qquad (II)$$

wherein R represents an alkyl group, a process for producing said alkoxysilanes characterized in that the reaction of the chlorosilane and the alcohol is performed in the co-presence of (a) an inert low boiling solvent having a boiling point lower than the boiling point of the objective alkoxysilane represented by general formula (III) and a difference in boiling point is not smaller than 4° C. and (b) an inert high boiling solvent having a boiling point higher than the boiling point of the objective alkoxysilane and a difference in boiling point is not smaller than 4° C.

2 Claims, No Drawings

PROCESS FOR PRODUCING ALKOXYSILANES

The present application claims the priority of Japanese Patent Applications Serial No. 62-145378 filed on June 12, 1987.

BACKGROUND OF THE INVENTION

The present invention relates to a process for producing alkoxysilanes and more particularly, to a process for producing alkoxysilanes which can provide alkoxysilanes having at least one Si—H bond in the molecule thereof in a high yield.

As a process for producing alkoxysilanes having an Si-H bond in the molecule thereof, there is hitherto known a process which comprises chlorosilanes having the Si—H bond with alcohols. According to this process, the reaction proceeds as shown by the following reaction scheme:

$$(CH_3)_aH_bSiCl_{4-a-b}+(4-a-b)ROH \rightarrow (CH_3)_aH_bSi(OR)_{4-a-b}+(4-a-b)HCl$$

Namely, as is clear from the reaction scheme described above, hydrogen chloride is by-produced together with the alkoxysilane having Si-H bonds but the by-produced hydrogen chloride is intermingled with the produced alkoxysilane. It is not only difficult to remove this hydrogen chloride but also the Si—H bond portion of the alkoxysilane is alkoxylated due to its presence. As a result, yield of the alkoxysilane having the Si-H bond is reduced. Giving an example, in the case of producing methyldimethoxysilane from methyldichlorosilane and methanol, the produced methyldimethoxysilane is methoxylated into methyltrimethoxysilane by the presence of the hydrogen chloride by-produced. As the result, yield of the objective methyldimethoxysilane is reduced.

In order to prevent such a reduction in yield of the alkoxysilane, there is known a method for preventing alkoxylation of the Si-H bond which comprises previously incorporating amines such as pyridine, etc. into the reaction system thereby to neutralize the by-produced hydrogen chloride.

In such a method, however, a step of filtering and separating the formed amine hydrochloride fine powders is required. Further a step of recovering the amine from the separated amine hydrochloride becomes complicated. Furthermore, the method described above involves problems that a part of the alkoxysilane produced is absorbed into the amine hydrochloride and the system must be subjected to a treatment for washing with large quantities of solvents in order to recover the alkoxysilane, and the like. Such problems are disadvantageous from an industrial viewpoint. Further, for similar purposes, in a process for producing the alkoxysilane using ethylenediamine or sodium methoxide, the Si—H bond in the alkoxysilane is alkoxylated so that the process is not practical.

Further as a method other than those described above for producing the allkoxysilane by the reaction of chlorosilanes and alcohols, there is provided, for example, a method which comprises introducing alcohols into liquid chlorosilanes without contacting the alcohols with chlorosilanes presented in the gaseous phase, stepwise proceeding alkoxylation of the chlorosilanes and performing the final esterification step with heating (Published Unexamined Japanese Patent Application No. 95518/1979).

As is evident from examples of the published application supra, however, such a method cannot provide the objective alkoxysilane having an Si—H bond in high yield unless a reaction apparatus equipped with a reflux condenser cooled to −48° to −82° C. is necessarily used. That is, such a technique contemplates to increase the yield, by performing the final esterification with heating thereby to increase a rate of generating hydrogen chloride and a rate of removing hydrogen chloride and as the result, to shorten the contact time of the formed alkoxysilane having an Si—H bond with hydrogen chloride and deeply cool the condenser, thus preventing the loss of the unreacted chlorosilane and the formed alkoxysilane by being accompanied with hydrogen chloride. However, it is necessary to deeply cool the condenser, as described above so that energy consumption is very large and such is industrially disadvantageous.

SUMMARY OF THE INVENTION

An object of the present invention is to eliminate the foregoing problems and provide a process for producing the alkoxysilane having an Si—H bond.

As a result of extensive investigations to achieve the object described above, the present inventors have found that in the case of the reaction of chlorosilanes having an Si-H bond with alcohols is conducted in the co-presence of a solvent having a boiling point higher than and a solvent having a boiling point lower than the boiling point of the objective alkoxysilane, the alkoxysilane having an Si—H bond can be obtained in a high yield.

Namely, the process for producing the alkoxysilane in accordance with the present invention is directed to a process for producing an alkoxysilane represented by general formula (III):

$$(CH_3)_aH_bSi(OR)_cCl_{4-(a+b+c)} \qquad (III)$$

wherein a represents a number of 0 to 2, b represents a number of 1 to 3, c represents a number of 0 to 2, the sum of a+b+c represents a number of not greater than 4 which comprises reacting a chlorosilane represented by general formula (I):

$$(CH_3)_aH_bSiCl_{4-(a+b)} \qquad (I)$$

wherein a and be have the same meanings as described above and a+b represents a number of less than 4, with an alcohol represented by general formula (II):

$$ROH \qquad (II)$$

wherein R represents an alkyl group, and is characterized in that the reaction of the chlorosilane and the alcohol is performed in the co-presence of (a) an inert low boiling solvent having a boiling point lower than the boiling point of the objective alkoxysilane represented by general formula (III) and a difference in boiling point is not smaller than 4° C. and (b) an inert high boiling solvent having a boiling point higher than the boiling point of the objective alkoxysilane and a difference in boiling point is not smaller than 4° C.

DETAILED DESCRIPTION OF THE INVENTION

The chlorosilanes used in the present invention contains at least one Si—H bond and is represented by general formula (I) described above. As the chlorosilanes, mention may be made of, for example, monochlorosilane, dichlorosilane, trichlorosilane, methyldichlorosilane and dimethyl-chlorosilane.

The alcohols used in the present invention are those shown in general formula (II) and examples include methanol, ethanol, n-propanol, isopropanol, n-butanol, isobutanol and the like. Among them, methanol and ethanol that the reactivity of the formed alkoxysilane is excellent are particularly preferred for the process of the present invention.

With respect to the amount of the alcohol to be reacted with the chlorosilane, the alcohol is used in a theoretical amount necessary for alkoxylating a part or whole of the Si—Cl bond in the chlorosilane, or in a slightly excess of amount.

In the present invention, upon the reaction of the aforesaid chlorosilane with the alcohol to produce the alkoxysilane, the reaction is conducted in such a state that the solvent having a boiling point lower than the boiling point of the alkoxysilane described above and a difference in boiling point is 4° C. or greater (hereafter simply referred to as "low boiling solvent") and the solvent having a higher boiling point and a difference in boiling point is 4° C. or greater (hereafter simply referred to as "high boiling solvent") are co-present in the reaction system.

The low boiling solvent and the high boiling solvent used herein both effectively act to stabilize the formed alkoxysilane in the reaction system, especially, to protect the Si-H bond of the alkoxysilane. As such high boiling solvent and low boiling solvent, there are both used those inert to the reaction between the chlorosilane and the alcohol and having a difference from the boiling point of the formed alkoxysilane being 4° C. or greater. In case that the difference in boiling point between these solvents is smaller than 4° C., it becomes difficult to separate the formed alkoxysilane from the aforesaid solvents after completion of the reaction.

Such low boiling solvent and high boiling solvent are appropriately selected depending upon the boiling point of the alkoxysilane to be produced and provided for use. As the low boiling solvents that can be used, mention may be made of, for example, hydrocarbon solvents such as n-pentane, n-hexane, cyclohexane and benzene, etc.; halogenated hydrocarbon solvents such as methylene chloride, chloroform, etc.; ethereal solvents such as diethyl ether, tetrahydrofuran, etc. As the high boiling solvents that can be used, mention may be made of, for example, n-heptane, cyclohexane, decaline, benzene, toluene, xylene, ethylbenzene and the like.

An amount of the low boiling solvent to be used is preferably 10 to 200 parts by weight, more preferably 20 to 10 parts by weight, based on 100 parts by weight of the chlorosilane. In case that the amount of the solvent to be used is less than 10 parts by weight, the yield of the alkoxysilane is poorly improved. Even when the solvent is used in an amount exceeding 200 parts by weight, the yield does not change. Rather, a volume yield decreases and production costs increase.

An amount of the high boiling solvent is preferably 20 to 200 parts by weight, more preferably 20 to 100 parts by weight, based on 100 parts by weight of the chlorosilane. In case that the amount of the solvent to be used is outside this range, the yield of the objective alkoxysilane decreases.

The amounts of the low boiling solvent and the high boiling solvents to be used are as described above. A ratio of the low boiling solvent to the high boiling solvent varies depending upon kind of solvents used. The low boiling solvent and the high boiling solvent are generally preferably used in a weight ratio of 1 : 10 to 10 : 1, more preferably in a range of 1 : 1 to 3 : 1.

In the present invention, the low boiling solvent and the high boiling solvent are allowed to be co-present in the reaction system. The reaction system as used herein not only means in a reaction vessel but also includes a condenser connected with the reaction vessel. Further upon the reaction, a part of the formed hydrogen chloride remains in the reaction vessel; in this case, weak amines such as pyridine in a small amount, etc. can be used to neutralize the hydrogen chloride.

Conditions for the reaction between the chlorosilane and the alcohol in the present invention are not particularly limited but the reaction can be conducted at normal temperature or by heating at a desired temperature up to the reflux temperature of the low boiling solvent.

After completion of the reaction, the objective alkoxysilane, the low boiling solvent and the high boiling solvent can be independently separated and recovered by distillation. The recovered low boiling solvent and high boiling solvent can be re-used.

The present invention is applicable to the process for producing the alkoxysilane represented by general formula (III), for example, monomethoxysilane, dimethoxysilane, trimethoxysilane, methyldimethoxysilane and dimethylmethoxysilane or other alkoxysilanes corresponding thereto. Further by controlling the amount of the alcohol, the present invention is also applicable to the process for producing chlorodimethoxysilane, dichloromethoxysilane, methylchloromethoxysilane and other partially alkoxylated chlorosilanes corresponding thereto.

According to the process of the present invention, the alkoxysilane having an Si—H bond can be obtained in a high yield, without setting particularly limited production conditions, for example, such as deeply cooling a reflux condenser connected to a reaction vessel, etc. Its purification is also simple.

The alkoxysilane obtained by the process of the present invention contains the Si—H bond and alkoxy group in the molecule thereof and therefore, has a good reactivity and is useful as an intermediate for preparing various organic silicon compounds or silicon functional polymers, etc.

EXAMPLES OF THE INVENTION

Hereafter the present invention will be described in more detail, with reference to the examples and comparative examples, wherein parts are all by weight, unless otherwise indicated.

EXAMPLES 1 THROUGH 3

In a reaction vessel equipped with a cooler, a stirrer, a tube capable of introducing methanol beneath the liquid surface of the charged chlorosilane and solvent and a thermometer were charged methyldichlorosilane, n-pentane and toluene in amounts shown in Table 1. Thereafter, methanol was fed through the introducing tube at a rate of 1 part/min, while stirring at normal temperature to be homogeneous. After an amount of methanol fed reached a primary feeding amount shown in Table 1, the feeding was once discontinued. Then, the content of the reaction vessel was heated to about 40° C. to reflux for an hour while keeping the temperature of the cooler at −10° C. using methanol as a coolant. Then, after the remaining methanol was further fed at the same feeding rate, heating was continued at 40° C. for 20 minutes to complete the reaction.

Yield of the formed methoxysilane (the peak of the solvent was neglected) was determined by gas chromatography. The results are shown in Table 1. The reaction product was distilled, whereby methyldimethoxysilane having a boiling point of 61° C. and methyltrimethoxysilane having a boiling point of 102° C. were isolated from each other.

TABLE 1

|  | Example 1 | Example 2 | Example 3 |
|---|---|---|---|
| Amount Charged (part): |  |  |  |
| Methyldichlorosilane | 115 | 115 | 115 |
| n-Pentane | 38 | 115 | 77 |
| Toluene | 77 | 115 | 38 |
| Amount of Methanol Fed (part): |  |  |  |
| Total amount | 70 | 70 | 70 |
| Primary feeding amount |  | 32 | 32 |
| Yield (%): |  |  |  |
| Methyldimethoxysilane | 79 | 83 | 90 |
| Methyltrimethoxysilane | 16 | 12 | 6 |

EXAMPLES 4 THROUGH 6

A reaction between methyldichlorosilane and methanol was carried out in a manner similar to Example 1 except that kinds and charged amounts of the low boiling solvent and the high boiling solvent were used as shown in Table 2. However, the reflux temperature was set at 45° C. in Example 4 because the low boiling point used was different. As the result of the reaction, yield of methoxysilane was as shown in Table 2.

TABLE 2

|  | Example 4 | Example 5 | Example 6 |
|---|---|---|---|
| Solvent (part): |  |  |  |
| Methylene chloride | 40 | — | — |
| n-Pentane | — | 60 | — |
| Diethyl ether | — | — | 40 |
| Benzene | 75 | — | — |
| Xylene | — | 60 | 75 |
| Yield (%): |  |  |  |
| Methyldimethoxysilane | 77 | 81 | 80 |
| Methyltrimethoxysilane | 15 | 13 | 14 |

COMPARATIVE EXAMPLES 1 THROUGH 5

A reaction between methyldichlorosilane and methanol was carried out in a manner similar to Example 1 except that no solvent was used or either the high boiling solvent or the low boiling solvent was used and the reaction was carried out at a reflux temperature corresponding to the respective solvent. In Comparative Examples 1 and 2, the high boiling solvent was used; in Comparative Examples 3 and 4, the low boiling point was used; and in Comparative Example 5, any solvent was not used. Kinds and amounts of the solvent used and yield of the obtained silane are shown in Table 3.

TABLE 3

|  | Comparative Example 1 | Comparative Example 2 | Comparative Example 3 | Comparative Example 4 | Comparative Example 5 |
|---|---|---|---|---|---|
| Solvent (part): |  |  |  |  |  |
| Toluene | 77 | — | — | — | — |
| Benzene | — | 77 | — | — | — |
| Methylene chlorie | — | — | 77 | — | — |
| n-Pentane | — | — | — | 77 | — |
| Yeild (%): |  |  |  |  |  |
| Methyldimethoxysilane | 63 | 67 | 66 | 70 | 40 |
| Methyltrimethoxysilane | 35 | 28 | 31 | 28 | 57 |

EXAMPLE 7 AND COMPARATIVE EXAMPLES 6 THROUGH 8

Trimethoxysilane having a boiling point of 84° C. and tetramethoxysilane having a boiling point of 121° C. were obtained in a manner similar to Example 1 except that trichlorosilane, solvent and methanol were used in amounts shown in Table 4. Yields are shown in Table 4.

TABLE 4

|  | Example 7 | Comparative Example 6 | Comparative Example 7 | Comparative Example 8 |
|---|---|---|---|---|
| Charged Amount (part): |  |  |  |  |
| Trichlorosilane | 135.5 | 135.5 | 135.5 | 135.5 |
| n-Pentane | 135.5 | 135.5 | — | — |
| Xylene | 90 | — | 135.5 | — |
| Amount of Methanol Fed (part): |  |  |  |  |
| Total amount | 106 | 106 | 106 | 106 |
| primary feeding amount | 48 | 48 | 48 | 48 |
| Yield (%): |  |  |  |  |
| Trimethoxysilane | 90 | 74 | 72 | 65 |
| Tetramethoxysilane | 7 | 22 | 25 | 27 |

EXAMPLE 8

Methyldiethoxysilane having a boiling point of 95° C. (yield, 88%) and methyldiethoxysilane having a boiling point of 143° C. (yield, 7%) were obtained in a manner similar to Example 1 except that 38 parts of decaline were used as the high boiling solvent, ethanol was used in place of methanol, its feeding amount was 1.5 parts/min., the amount of ethanol was 46 parts as a primary feeding amount and 101 parts in total.

As is clear from Tables 1 through 4, in Examples 1 through 8 in which the solvent having a boiling point lower than and the solvent having a boiling point higher than, the boiling point of the formed methyldimethoxysilane or trimethoxysilane (both have a difference in boiling point from the aforesaid silane is 4° C. or greater) are co-present in the reaction system, the objective silanes having an Si—H bond can be obtained in yields of 77 to 90%. To the contrary, in the case of Comparative Examples 1, 4, 6 and 7 in which the reaction was conducted in the presence of either solvent, yields were 63 to 74%. In the case of Comparative Examples 5 and 8 in which no solvent was used, the yield was 40% and 65%, respectively. In the comparative examples, the yields were greatly reduced as compared to the examples.

Namely, from these results, it is understood that not only in the case of using no solvent but also merely in the presence of a solvent, upon the reaction between the chlorosilane having an Si—H bond and the alcohol, the alkoxysilane having an Si—H bond cannot be obtained in a satisfactory yield.

While the invention has been described in detail and with reference to specific embodiments thereof, it is apparent to one skilled in the art that various changes and modifications can be made therein without departing from the spirit and the scope of the present invention.

What is claimed is:

1. In a process for producing an alkoxysilane represented by general formula (III):

$$(CH_3)_a H_b Si(OR)_c Cl_{4-(a+b+c)} \quad (III)$$

wherein a represents a number of 0 to 2, b represents a number of 1 to 3, c represents a number of 0 to 2, the sum of a+b+c represents a number of not greater than 4 which comprises reacting a chlorosilane represented by general formula (I):

$$(CH_3)_a H_b SiCl_{4-(a+b)} \quad (I)$$

wherein a and b have the same meanings as described above and a+b represents a number of less than 4, with an alcohol represented by general formula (II):

$$ROH \quad (II)$$

wherein R represents an alkyl group, the process for producing said alkoxysilanes characterized in that the reaction of said chlorosilane and said alcohol is performed in the copresence of (a) an inert low boiling solvent having a boiling point lower than the boiling point of the objective alkoxysilane represented by general formula (III) and a difference in boiling point is not smaller than 4° C. and (b) an inert high boiling solvent having a boiling point higher than the boiling point of the objective alkoxysilane and a difference in boiling point is not smaller than 4° C.

2. The process as claimed in claim 1 wherein R in ROH shown by general formula (II) described above is a methyl group or an ethyl group.

* * * * *